US011559196B2

(12) United States Patent
Okayama et al.

(10) Patent No.: US 11,559,196 B2
(45) Date of Patent: Jan. 24, 2023

(54) FLEXIBLE ENDOSCOPE, AND ENDOSCOPE SYSTEM EQUIPPED WITH SAME

(71) Applicants: OSAKA UNIVERSITY, Osaka (JP); SUMITA OPTICAL GLASS, Inc., Saitama (JP)

(72) Inventors: Keita Okayama, Osaka (JP); Shinsuke Nanto, Osaka (JP); Hiroya Hoshi, Saitama (JP)

(73) Assignees: OSAKA UNIVERSITY, Osaka (JP); SUMITA OPTICAL GLASS, INC., Saitama (JP)

( * ) Notice: Subject to any disclaimer, the term of this patent is extended or adjusted under 35 U.S.C. 154(b) by 479 days.

(21) Appl. No.: 16/494,478

(22) PCT Filed: Mar. 14, 2018

(86) PCT No.: PCT/JP2018/009971
§ 371 (c)(1),
(2) Date: Sep. 16, 2019

(87) PCT Pub. No.: WO2018/168926
PCT Pub. Date: Sep. 20, 2018

(65) Prior Publication Data
US 2020/0015671 A1 Jan. 16, 2020

(30) Foreign Application Priority Data
Mar. 17, 2017 (JP) .............................. JP2017-053637

(51) Int. Cl.
*A61B 1/06* (2006.01)
*A61B 1/005* (2006.01)
(Continued)

(52) U.S. Cl.
CPC ............ *A61B 1/3137* (2013.01); *A61B 1/005* (2013.01); *A61B 1/0661* (2013.01); *G02B 23/2469* (2013.01); *A61B 1/07* (2013.01)

(58) Field of Classification Search
CPC ....... A61B 1/3137; A61B 1/0661; A61B 1/07; G02B 23/2469
See application file for complete search history.

(56) References Cited

U.S. PATENT DOCUMENTS 5,073,048 A 12/1991 Adachi et al.
8,986,340 B2 * 3/2015 Drontle .............. A61M 25/0113
606/199

(Continued)

FOREIGN PATENT DOCUMENTS

JP H03-275030 A 12/1991
JP H09-164112 A 6/1997
(Continued)

*Primary Examiner* — Timothy J Neal
*Assistant Examiner* — William B Chou
(74) *Attorney, Agent, or Firm* — Pearne & Gordon LLP (57) ABSTRACT

A flexible endoscope of the present invention includes a catheter portion and a connection plug. The catheter portion includes an image guide, a light guide, and a catheter tube that surrounds the image guide and the light guide in a longitudinal direction, and the connection plug includes a hollow cover that accommodates the proximal end of the catheter tube, a flexible tube that protrudes from the hollow cover and through which the catheter tube is passed, a first connection terminal that is connected to the light guide extending from the proximal end of the catheter tube, and a second connection terminal that is connected to the image guide extending from the proximal end of the catheter tube. The image guide and the light guide are slidable inside the catheter tube, and at least one of the image guide and the light guide is arranged curved inside the hollow cover of the connection plug.

8 Claims, 8 Drawing Sheets

(51) Int. Cl.
  *A61B 1/07*    (2006.01)
  *A61B 1/313*   (2006.01)
  *G02B 23/24*   (2006.01)

(56) References Cited

U.S. PATENT DOCUMENTS

| | | |
|---|---|---|
| 2002/0120181 A1 | 8/2002 | Irion |
| 2004/0133073 A1 | 7/2004 | Berci et al. |
| 2004/0158159 A1 | 8/2004 | Seto et al. |
| 2009/0018397 A1* | 1/2009 | Scholly ................. A61B 1/128 600/178 |
| 2018/0228548 A1* | 8/2018 | Blumenkranz .... A61B 1/00165 |

FOREIGN PATENT DOCUMENTS

| | | |
|---|---|---|
| JP | 2004-229742 A | 8/2004 |
| JP | 2015-211739 A | 11/2015 |

* cited by examiner

FLEXIBLE ENDOSCOPE, AND ENDOSCOPE SYSTEM EQUIPPED WITH SAME

TECHNICAL FIELD

The present invention relates to a flexible endoscope and an endoscope system equipped with the same, and more specifically to a flexible endoscope that can be easily connected to a relay apparatus, and an endoscope system equipped with the same.

BACKGROUND ART

In recent years, various endoscopic technologies that can be used to perform diagnosis, an operation, and the like inside a human body have been developed.

In particular, a flexible endoscope called an angioscope or angioscope catheter is used to measure the properties, length, and/or stenosis rate of a lesion inside a blood vessel such as a coronary artery. Such an angioscope is designed to have an elongated shape with a very small axial diameter compared with a digestive endoscope to be used to perform diagnosis, an operation, and the like on digestive organs, for example, in order to facilitate forward movement and backward movement inside a blood vessel. Furthermore, the angioscope includes, at its distal end (i.e., a leading end of the endoscope that is the farthest from the hand of a doctor), at least two guide members, namely a light guide including an optical fiber that can be used to irradiate the outside thereof with light, and an image guide including an image fiber for image transmission to be used to transmit, to a doctor, image information obtained at the distal end.

In addition, the proximal ends of these two guides of the angioscope (i.e., a leading end of the endoscope that is the closest to the hand of a doctor) are connected to a relay apparatus, and the relay apparatus is electrically connected to a medical console having various information processing functions including functions for displaying, analyzing, and storing the transmitted image information.

It has been conventionally proposed that the two guides of the angioscope are connected to the relay apparatus by inserting connection terminals of the light guide and image guide extending from the angioscope into ports provided in the relay apparatus. However, with such a procedure in which connection terminals are individually connected, there is a concern that a connection operation will take an unnecessary amount of time, and the connection terminals of the guides will be mistaken and connected to the wrong ports.

Meanwhile, the image fiber for the image guide included in such an angioscope is obtained by bundling, or bundling and bonding or fusing, a plurality of fine glass fibers using a method known to those skilled in the art, or by extending the thus-obtained bundles. If care is not taken during connection to the relay apparatus, it is conceivable that these fibers will be damaged and the performance of the image fiber is thus impaired. Therefore, care also needs to be taken during connection to the relay apparatus.

SUMMARY OF THE INVENTION

Problem to be Solved by the Invention

The present invention was made in order to solve the foregoing problems, and it is an object thereof to provide a flexible endoscope that suppresses damage to fibers included in the image guide and the light guide and can be easily connected to a relay apparatus, and an endoscope system equipped with the flexible endoscope.

Means for Solving the Problem

The present invention provides a flexible endoscope comprising:
 a catheter portion; and
 a connection plug,
 wherein the catheter portion includes an image guide, a light guide, and a catheter tube that surrounds the image guide and the light guide in a longitudinal direction,
 the connection plug includes a hollow cover that accommodates a proximal end of the catheter tube, a flexible tube that protrudes from the hollow cover and through which the catheter tube is passed, a first connection terminal that is connected to the light guide extending from the proximal end of the catheter tube, and a second connection terminal that is connected to the image guide extending from the proximal end of the catheter tube,
 the image guide and the light guide are slidable inside the catheter tube,
 the first connection terminal and the second connection terminal protrude from the hollow cover of the connection plug substantially in parallel, and
 at least one of the image guide and the light guide is arranged curved inside the hollow cover of the connection plug.

In one embodiment, a level difference is formed between a leading end of the first connection terminal protruding from the hollow cover and a leading end of the second connection terminal protruding from the hollow cover.

In a further embodiment, the leading end of the second connection terminal is positioned farther than the leading end of the first connection terminal.

In one embodiment, at least one flange extending in a direction orthogonal to an arrangement direction of the first connection terminal and the second connection terminal is provided on an outer surface of the hollow cover.

In one embodiment, wherein at least one boss is provided on an inner surface of the hollow cover of the connection plug, and at least one of the light guide and the image guide circumvents the boss in the hollow cover and is thus arranged curved.

In one embodiment, in the hollow cover of the connection plug, the image guide is arranged curved and the light guide is substantially linearly arranged.

In one embodiment, in the connection plug, a portion on the first connection terminal side and a portion on the second connection terminal side differ in thickness.

In one embodiment, the flexible endoscope is an angioscope.

The present invention also provides an endoscope system comprising:
 the above flexible endoscope;
 a relay apparatus that accommodates and is connected to the first connection terminal and the second connection terminal of the flexible endoscope; and
 a console that is connected to the relay apparatus via a cable for transmitting image information.

Effects of the Invention

With the present invention, the connection to the relay apparatus can be made in a shorter period of time. In addition, a load applied to the fibers at the time of connecting and during use is reduced. This makes it possible to prevent the fibers inside the flexible endoscope from being damaged, and thus prevent the performance of the image guide and the light guide from being impaired.

BRIEF DESCRIPTION OF DRAWINGS

FIGS. 4A and 4B show enlarged views of the connection plug included in the flexible endoscope shown in FIG. 1. FIG. 4B is a top view of the connection plug.

FIG. 5A is a partially enlarged view of the connection plug shown in FIG. 4A, and FIG. 5B is a partially enlarged view of the connection plug shown in FIG. 4B.

FIGS. 7A and 7B show cross-sectional views of a catheter portion included in the flexible endoscope shown in FIG. 1 in a longitudinal direction.

MODES FOR CARRYING OUT THE INVENTION

Hereinafter, the present invention will be described in detail

1. Flexible Endoscope

Figure 1:
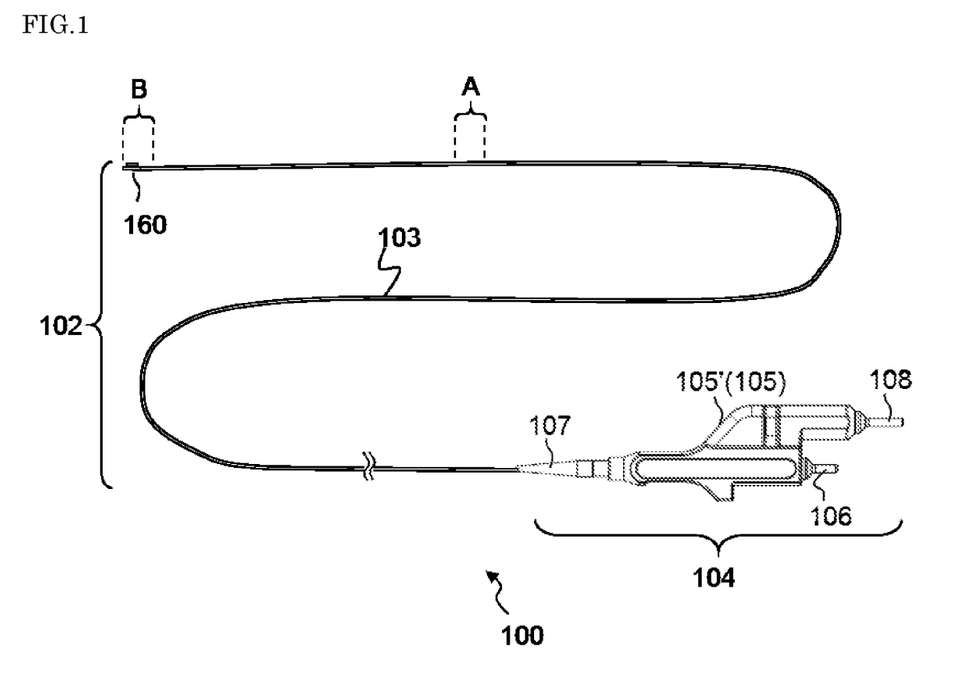
FIG. 1 is a diagram for illustrating an example of a flexible endoscope of the present invention.

FIG. 1 is a diagram for illustrating an example of a flexible endoscope of the present invention.

A flexible endoscope 100 includes a catheter portion 102 and a connection plug 104. The catheter portion 102 is flexible as a whole, and includes one or more image fibers for transmitting image information obtained at the distal end to a doctor, a light guide including a plurality of optical fibers, and a catheter tube 103 that extends in the longitudinal direction and surrounds the image guide and the light guide. Both the image guide and the light guide are not fixed inside the catheter tube 103 and they are slidable individually. The catheter portion 102 preferably has a substantially columnar shape and includes an end fitting 160 at the distal end of the catheter tube 103.

The term "distal" as used herein is used to indicate a position of an instrument or apparatus such as an endoscope and refers to a portion of the instrument or apparatus that is located away from a doctor when the doctor is using the instrument or apparatus. The term "proximal" as used herein is used to indicate a position of an instrument or apparatus and refers to a portion of the instrument or apparatus that is located close to a doctor when the doctor is using the instrument or apparatus.

In FIG. 1, the light guide extending from the proximal end of the catheter tube 103 included in the catheter portion 102 is connected to a first connection terminal 106 inside the connection plug 104. The image guide extending from the proximal end of the catheter tube 103 included in the catheter portion 102 is connected to a second connection terminal 108 inside the connection plug 104.

Furthermore, in the connection plug 104 shown in FIG. 1, the proximal end of the catheter tube 103 is accommodated together with the proximal ends of the image guide and the light guide in two covers 105 and 105' that are molded so as to have a hollow portion. The first connection terminal 106 and the second connection terminal 108 are arranged to protrude from the hollow covers 105 and 105' of the connection plug 104 and extend substantially in parallel. Here, the catheter tube 103 is passed through a flexible tube 107 attached to the hollow covers 105 and 105', and accommodated and fixed inside the hollow covers 105 and 105'. It is preferable that the flexible tube 107 is made of a material having appropriate elasticity, and specific examples of the material include silicone rubber, natural or synthetic rubber, polyimide, nylon, polyethylene terephthalate, and polyamide.

1.1 Connection Plug of Flexible Endoscope

With the flexible endoscope of the present invention, at least one of the image guide and the light guide is arranged curved inside the hollow covers of the connection plug.

Figure 2:
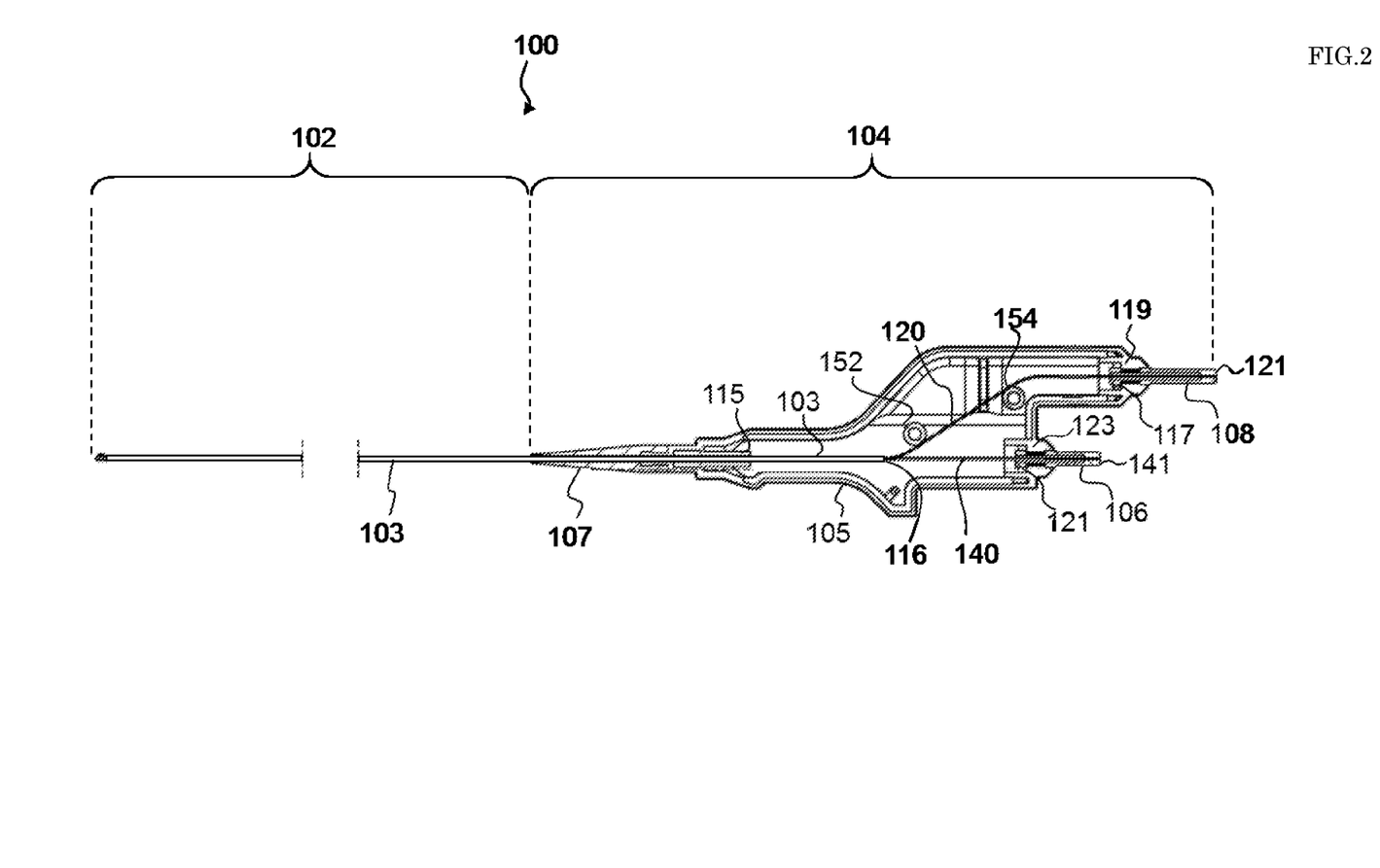
FIG. 2 is a partially cutaway cross-sectional view of the flexible endoscope shown in FIG. 1 for illustrating the internal structure of a connection plug of the flexible endoscope.

FIG. 2 is a partially cutaway cross-sectional view of the flexible endoscope shown in FIG. 1 for illustrating the internal structure of a connection plug of the flexible endoscope.

As shown in FIG. 2, a portion on the proximal end 116 side of the catheter tube 103 extends from the catheter portion 102 via the flexible tube 107 to the inside of the hollow cover 105 of the connection plug 104, and the proximal end 116 is accommodated inside the hollow cover 105. The material of the hollow cover 105 is not particularly limited, but is preferably a synthetic resin such as ABS (acrylonitrile-butadiene-styrene) resin, epoxy resin, PTFE (polytetrafluoroethylene), nylon, polyethylene terephthalate, polyamide, or polyurethane because such resins are easy to mold.

Here, a portion of the outer circumference of the catheter tube 103, which extends to the inside of the hollow cover 105 via the flexible tube 107 and is accommodated inside the hollow cover 105, is fixed inside a throat portion 115 that has a predetermined length and is provided inside the hollow cover 105. Furthermore, the proximal end 116 of the catheter tube 103 ends inside the hollow cover 105, and an image guide 120 and a light guide 140 are exposed and branch off from the catheter tube 103 at the proximal side than the proximal end 116 of the catheter tube 103, and are oriented in respective predetermined directions as described later. The branching image guide 120 and light guide 140 are respectively connected to two ferrules (i.e., the second connection terminal 108 and the first connection terminal 106).

In an embodiment of the present invention, the image guide 120 is passed through the second connection terminal 108 and arranged such that its proximal end 121 is substantially flush with a leading end 112 of the second connection terminal 108. Here, the proximal end of the image guide 120 is bonded inside the second connection terminal 108, and the second connection terminal 108 is fixed by a terminal arrangement portion 119 provided in the hollow cover 105. The proximal end of the image guide 120 is thus fixed by the hollow cover 105. On the other hand, the light guide 140 is passed through the first connection terminal 106 and arranged such that its proximal end 141 is substantially flush with a leading end 110 of the first connection terminal 106. Here, the proximal end of the light guide 140 is bonded inside the first connection terminal 106, and the first connection terminal 106 is fixed by a terminal arrangement portion 123 provided in the hollow cover 105. The proximal end of the light guide 140 is thus fixed by the hollow cover 105. Since the image guide 120 and the light guide 140 extend such that the proximal ends 121 and 141 are located at such positions inside the connection terminals 108 and 106, connection loss (e.g., attenuation of light amount) that occurs between the connection terminals 108 and 106 and a relay apparatus to which the flexible endoscope can be connected via the connection plug can be reduced.

Furthermore, in the first connection terminal 106 and the second connection terminal 108, ferrule flange portions 117 and 121 that the first connection terminal 106 and the second connection terminal 108 are respectively provided with are locked to the terminal arrangement portions 119 and 123 of the hollow cover 105. This makes it possible to prevent the first connection terminal 106 and the second connection terminal 108 from coming loose from the hollow covers 105 and 105' of the connection plug 104 shown in FIG. 1.

FIG. 2 is referred to again. In the embodiment shown in FIG. 2, the hollow cover 105 includes two bosses 152 and 154 that are protrusions with a cylindrical shape, for example, and the image guide 120 extending from the proximal end 116 of the catheter tube 103 circumvents these bosses 152 and 154 and is oriented toward the second connection terminal 108. Here, it should be noted that the image guide 120 is arranged in the periphery of the bosses 152 and 154 and between the bosses 152 and 154 in the hollow cover 105 in a state in which tension is not applied thereto (i.e., in a non-tight manner). In FIG. 2, the image guide 120 is instead arranged in the periphery of the bosses 152 and 154 and between the bosses 152 and 154 in a loose manner (e.g., over a length longer than the shortest distance) to circumvent the bosses 152 and 154.

The term "curved" as used herein refers to a state in which the image guide and/or the light guide included in the flexible endoscope of the present invention is arranged in the connection plug in a loose manner over a sufficient length in a state in which tension is not applied thereto.

In the present invention, the degree of "curve" (e.g., length) set for the image guide and/or the light guide inside the connection plug is not particularly limited, and can be selected by those skilled in the art as appropriate depending on the size of the hollow covers, or the axial diameters of the image guide and the light guide, for example.

With the present invention, the catheter tube, which extends to the inside of the hollow covers via the flexible tube and is accommodated inside the hollow covers, is fixed inside the throat portion 115 provided inside the hollow cover 105 as described above. In contrast, with the present invention, the image guide and the light guide are slidable inside the catheter tube, and at least one of the image guide and the light guide is "curved" in the above-described manner and arranged inside the hollow covers. Due to these configurations of the flexible endoscope of the present invention, the image guide and/or the light guide can slide inside the flexible tube according to the "curve" inside the connection plug even if an unexpected load is applied to the image guide and/or the light guide inside the connection plug when the connection plug is connected to the relay apparatus or the flexible endoscope is used, thus making it possible to avoid the occurrence of excessive tension or bending in the image guide and/or the light guide inside the connection plug. As a result, a load applied to the fibers included in the image guide or light guide is reduced, thus making it possible to prevent the fibers inside the flexible endoscope from being damaged, and thus prevent the performance of the image guide and the light guide from being impaired.

It should be noted that, in the embodiment shown in FIG. 2, the two bosses 152 and 154 are provided inside the hollow cover 105, but there is no limitation on the number of bosses, and it is preferable that at least one boss is provided inside the hollow cover. The boss 152 shown in FIG. 2 is provided near a position located on the downstream side (proximal side) with respect to the proximal end 116 of the catheter tube 103 from which the image guide 120 and the light guide 140 branch off, and is provided at a position located, with respect to the branch point, on a side where the separation of the image guide 120 and the light guide 140 is prevented, that is, a position located on the proximal side with respect to point A such that the image guide 120 is arranged between the boss 152 and the light guide 140. The boss 152 arranged in this manner serves to prevent the image guide 120 from being excessively bent due to the image guide 120 and the light guide 140, which extend from the proximal end of the catheter tube 103, branching off at large angles, and prevent the catheter tube 103 from splitting from the proximal end of the tube.

In the embodiment shown in FIG. 2, the image guide 120 is arranged curved inside the hollow cover 105 of the connection plug 104 as described above, whereas the light guide 140 is substantially linearly arranged. The present invention is not limited to only such an arrangement. For example, the image guide and the light guide may be arranged inside the hollow covers of the connection plug as described below.

Figure 3A:
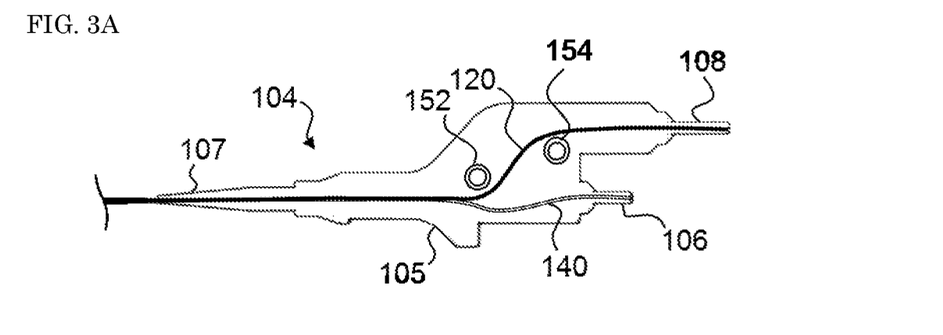
FIGS. 3A, 3B and 3C show schematic cross-sectional views for illustrating other examples of the arrangement of an image guide and a light guide inside the connection plug included in the flexible endoscope of the present invention.
Figure 3B:
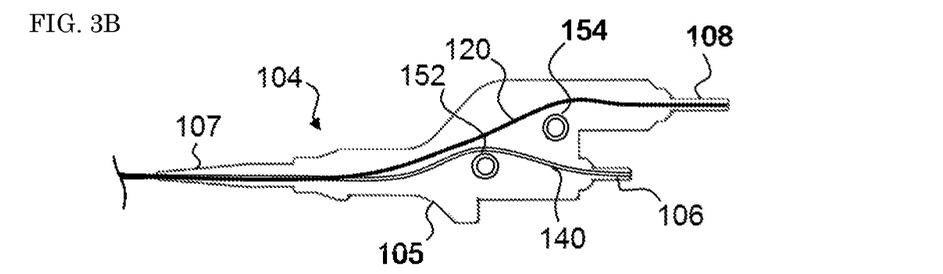
Figure 3C:
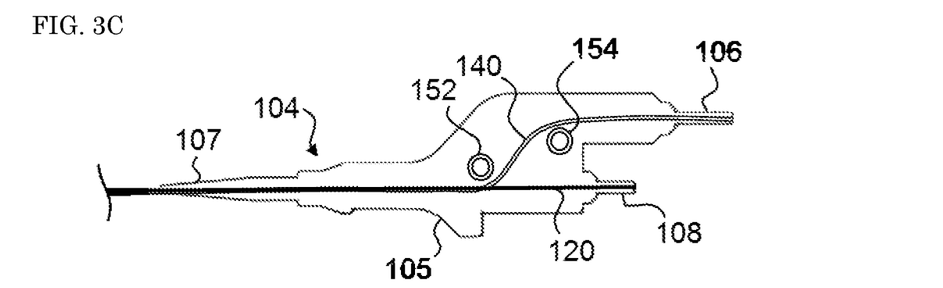

FIGS. 3A, 3B, and 3C show schematic cross-sectional views for illustrating other examples of the arrangement of the image guide and the light guide inside the connection plug included in the flexible endoscope of the present invention. It should be noted that, in FIGS. 3A, 3B, and 3C, the illustration of the catheter portion and the catheter tube of the flexible endoscope is omitted for simplification.

With the present invention, a configuration as shown in FIG. 3A may be adopted in which the image guide 120 and the light guide 140 are arranged on the same side with respect to the boss 152 (below the boss 152 in FIG. 3A) inside the hollow cover 105 of the connection plug 104, and regarding the boss 154, the image guide 120 is arranged above the boss 154 while the light guide 140 is arranged below the boss 154, and the image guide 120 and the light guide 140 are respectively connected to the second connection terminal 108 and the first connection terminal 106. In FIG. 3A, this arrangement results in a state in which both the image guide 120 and the light guide 140 are curved inside the hollow cover 105. Furthermore, with this arrangement, a state in which both the image guide 120 and the light guide 140 are not fixed inside the flexible tube 107 is maintained.

Therefore, with the arrangement shown in FIG. 3A, the image guide 120 and the light guide 140 can slide individually inside the flexible tube 107 according to the "curve" inside the connection plug 104, thus making it possible to avoid the occurrence of excessive tension or bending in the image guide 120 and the light guide 140 inside the connection plug 104.

Alternatively, with the present invention, a configuration as shown in FIG. 3B may be adopted in which the image guide 120 and the light guide 140 are arranged on the same side with respect to the boss 152 (above the boss 152 in FIG. 3B) inside the hollow cover 105 of the connection plug 104, and regarding the boss 154, the image guide 120 is arranged above the boss 154 while the light guide 140 is arranged below the boss 154, and the image guide 120 and the light guide 140 are respectively connected to the second connection terminal 108 and the first connection terminal 106. In FIG. 3B, this arrangement results in a state in which both the image guide 120 and the light guide 140 are curved inside the hollow cover 105. Furthermore, with this arrangement, a state in which both the image guide 120 and the light guide 140 are not fixed inside the flexible tube 107 is maintained.

Therefore, with the arrangement shown in FIG. 3B, the image guide 120 and the light guide 140 can slide individually inside the flexible tube 107 according to the "curve" inside the connection plug 104, thus making it possible to avoid the occurrence of excessive tension or bending in the image guide 120 and the light guide 140 inside the connection plug 104.

Alternatively, with the present invention, a configuration as shown in FIG. 3C may be adopted in which the image guide 120 and the light guide 140 are arranged on the same side with respect to the boss 152 (below the boss 152 in FIG. 3C) inside the hollow cover 105 of the connection plug 104, and regarding the boss 154, the image guide 120 is arranged below the boss 154 while the light guide 140 is arranged above the boss 154, and the image guide 120 and the light guide 140 are respectively connected to the second connection terminal 108 and the first connection terminal 106. In FIG. 3C, this arrangement results in a state in which the light guide 140 is curved inside the hollow cover 105. Furthermore, with this arrangement, a state in which both the image guide 120 and the light guide 140 are not fixed inside the flexible tube 107 is maintained.

Therefore, with the arrangement shown in FIG. 3C, the light guide 140 can slide inside the flexible tube 107 according to the "curve" inside the connection plug 104, thus making it possible to avoid the occurrence of excessive tension or bending in the light guide 140 inside the connection plug 104.

As described above, in the present invention, the image guide 120 and the light guide 140 may be arranged as shown in any of FIG. 2 and FIGS. 3A, 3B, and 3C. However, when the image guide 120 includes a single image fiber and the light guide 140 includes a plurality of optical fibers in the flexible endoscope of the present invention as described later, it is preferable that the image guide 120 is arranged curved inside the hollow cover 105 of the connection plug 104 and the light guide 140 is substantially linearly arranged as shown in FIG. 2. With this arrangement, the distal ends of the optical fibers of the light guide 140 with the same length simultaneously reach the leading end 110 of the first connection terminal 106, thus making it possible to reduce a variation in light amount loss that occurs between the light source in each optical fiber and the connection terminal. As a result, the attenuation of the amount of light emitted from the light guide at the distal end of the catheter portion can be prevented. On the other hand, damage to the image guide 120 can also be prevented.

Furthermore, in the arrangements shown in FIG. 2 and FIGS. 3A, 3B, and 3C, the "curve" of the image guide 120 and/or the light guide 140 may be formed in not only in the two-dimensional region (plane) extending in the longitudinal direction and the width direction of the hollow cover 105 but also in the three-dimensional region (space) extending in the longitudinal direction, the width direction, and the thickness direction of the hollow cover 105. Therefore, in FIG. 2 and FIGS. 3A, 3B, and 3C, the "curve" of the image guide 120 and/or the light guide 140 encompasses a curve formed in the thickness direction of the hollow cover 105, for example.

Figure 4A:
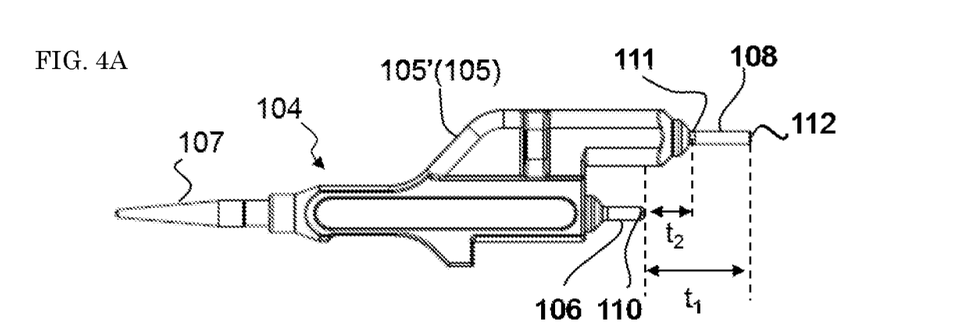
FIG. 4A is a plan view of the connection plug.
Figure 4B:
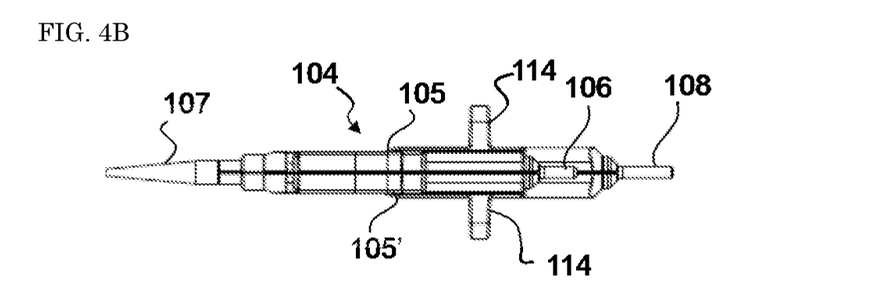

FIGS. 4A and 4B show enlarged views of the connection plug included in the flexible endoscope shown in FIG. 1. FIG. 4A is a plan view of the connection plug 104, FIG. 4B is a top view of the connection plug 104, and FIG. 4C is a partially enlarged view of the connection plug 104 shown in FIG. 4A. It should be noted that, in FIGS. 4A and 4B, the illustration of the catheter portion of the flexible endoscope is omitted.

It is preferable that the connection plug has a level difference provided between the leading end of the first connection terminal protruding from the hollow covers and the leading end of the second connection terminal protruding from the hollow covers in the flexible endoscope of the present invention.

For example, as shown in FIG. 4A, in the connection plug 104, the first connection terminal 106 (extending from the light guide 140 in FIG. 2) protrudes from the hollow cover 105 via a first dome-shaped protrusion 125, and the second connection terminal 108 (extending from the image guide 120 in FIG. 2) protrudes from the hollow cover 105 via a second dome-shaped protrusion 127.

In the embodiment shown in FIG. 4A, the leading end 112 of the second connection terminal 108 provided in the connection plug 104 is positioned farther than the leading end 110 of the first connection terminal 106. That is, in the present invention, a predetermined level difference $t_1$ is preferably provided between the leading end 110 of the first connection terminal 106 provided in the connection plug 104 and the leading end 112 of the second connection terminal 108 provided in the connection plug 104. The length (e.g., mm) of the level difference $t_1$ is not necessarily limited, but it is preferable to design the embodiment shown in FIG. 4A such that a level difference $t_2$ is provided between a base end 111 of the second connection terminal 108 and the leading end 110 of the first connection terminal 106, and the level difference $t_2$ has a length (e.g., mm) that satisfies a relationship $t_2>0$ (i.e., the base end of the second connection terminal 108 is located on the proximal side with respect to the leading end 110 of the first connection terminal 106). Due to this level difference $t_2$, the connection plug 104 does not sufficiently enter the relay apparatus even if the first connection terminal 106 and the second connection terminal 108 are improperly inserted into the receiving ports of the relay apparatus, thus making it possible to easily notice improper connection.

It is also preferable that, as shown in FIG. 4B, the connection plug 104 included in the flexible endoscope of the present invention includes flanges 114 that extend in a direction that is orthogonal to the arrangement direction of the first connection terminal 106 of the light guide and the second connection terminal 108 of the image guide (i.e., the axial direction of the first connection terminal 106 and the second connection terminal 108). The reason for this is that providing the relay apparatus with a locking mechanism for biasing the flanges 114 enables the connection plug 104 to be more easily inserted into and removed from the relay apparatus. It should be noted that each of the hollow covers 105 and 105' is provided with a single flange 104 in FIG. 4B, but the present invention is not necessarily limited to this configuration. For example, a configuration in which only one of the hollow covers 105 and 105' is provided with the flange 104 is also possible.

Figure 5A:
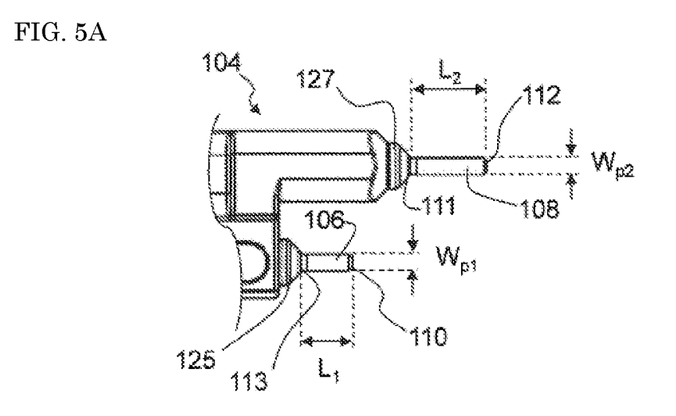
FIGS. 5A and 5B show partially enlarged views of the connection plug included in the flexible endoscope shown in FIGS. 4A and 4B.
Figure 5B:
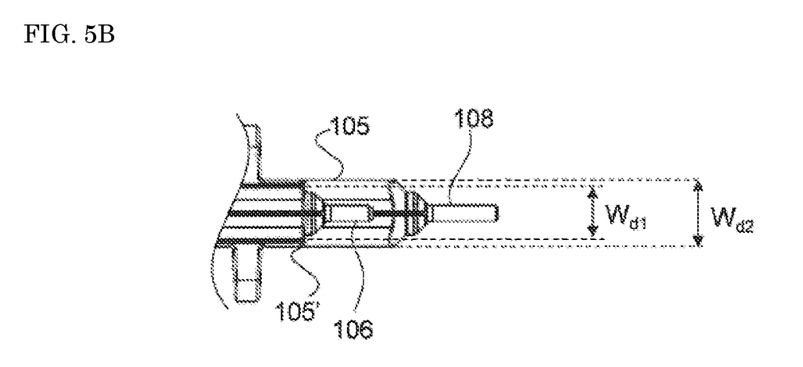

FIGS. 5A and 5B show partially enlarged views of the connection plug included in the flexible endoscope shown in FIGS. 4A and 4B. FIG. 5A is a partially enlarged view of the connection plug shown in FIG. 4A, and FIG. 5B is a partially enlarged view of the connection plug shown in FIG. 4B.

It is preferable that the connection plug 104 included in the flexible endoscope of the present invention is designed to satisfy at least one of the following items (1) to (3) in order to avoid improper insertion of the first connection terminal 106 and the second connection terminal 108 into the receiving ports of the relay apparatus.

(1) A description will be given with reference to FIG. 5A. When the leading end 112 of the second connection terminal 108 is positioned farther than the leading end 110 of the first connection terminal 106, the connection plug 104 may also be designed such that an axial diameter $W_{p2}$ of the second connection terminal 108 is larger than an axial diameter $W_{p1}$ of the first connection terminal 106 ($W_{p2} > W_{p1}$). The reason for this is that, when the relationship $W_{p2} > W_{p1}$ is satisfied, even if the second connection terminal 108 is mistakenly inserted into a receiving port of the relay apparatus that corresponds to the first connection terminal 106, the difference in the axial diameter makes insertion difficult.

(2) A description will be given with reference to FIG. 5A. The connection plug 104 may also be designed such that an axial length $L_2$ of the second connection terminal 108 is larger than an axial length $L_1$ of the first connection terminal 106 ($L_2 > L_1$). Here, the axial length $L_1$ of the first connection terminal 106 refers to a length (shortest distance) in the axial direction between a base end 113 and the leading end 110 of the first connection terminal 106, and the axial length $L_2$ of the second connection terminal 108 refers to a length (shortest distance) in the axial direction between a base end 111 and the leading end 112 of the second connection terminal 108. When the relationship $L_2 > L_1$ is satisfied, even if the second connection terminal 108 is mistakenly inserted into a receiving port of the relay apparatus that corresponds to the first connection terminal 106, the difference in the axial length makes it difficult to completely insert the second connection terminal 108 into the receiving port of the relay apparatus.

(3) A description will be given with reference to FIG. 5B. The connection plug 104 may also be designed such that a thickness $W_{d2}$ of a portion on the second connection terminal 108 side of an assembly of the hollow covers 105 and 105' is larger than a thickness $W_{d1}$ of a portion on the first connection terminal 106 side of the assembly of the hollow covers 105 and 105' ($W_{d2} > W_{d1}$). The reason for this is that, when the relationship $W_{d2} > W_{d1}$ is satisfied, even if the second connection terminal 108 is mistakenly inserted into a receiving port of the relay apparatus that corresponds to the first connection terminal 106, the difference in the thickness ($W_{d2}$ and $W_{d1}$) between the portions of the assembly of the hollow covers 105 and 105' that surround the connection terminals makes insertion difficult.

With the flexible endoscope of the present invention, employing a design as described in the items (1) to (3) above to the connection plug makes it possible to easily avoid improper insertion of the connection terminals of the connection plug into the relay apparatus.

Furthermore, regarding the embodiment shown in FIG. 4A, it is preferable to nullify, in advance, a risk that when the first connection terminal 106 and the second connection terminal 108 of the connection plug 104 are improperly inserted into the receiving ports of the relay apparatus, the leading end 112 of the second connection terminal 108, which is improperly inserted, will hit a component inside the relay apparatus that is provided for connection to the first connection terminal 106 and causes damage to that component. This point will be described with reference to FIG. 6.

Figure 6:
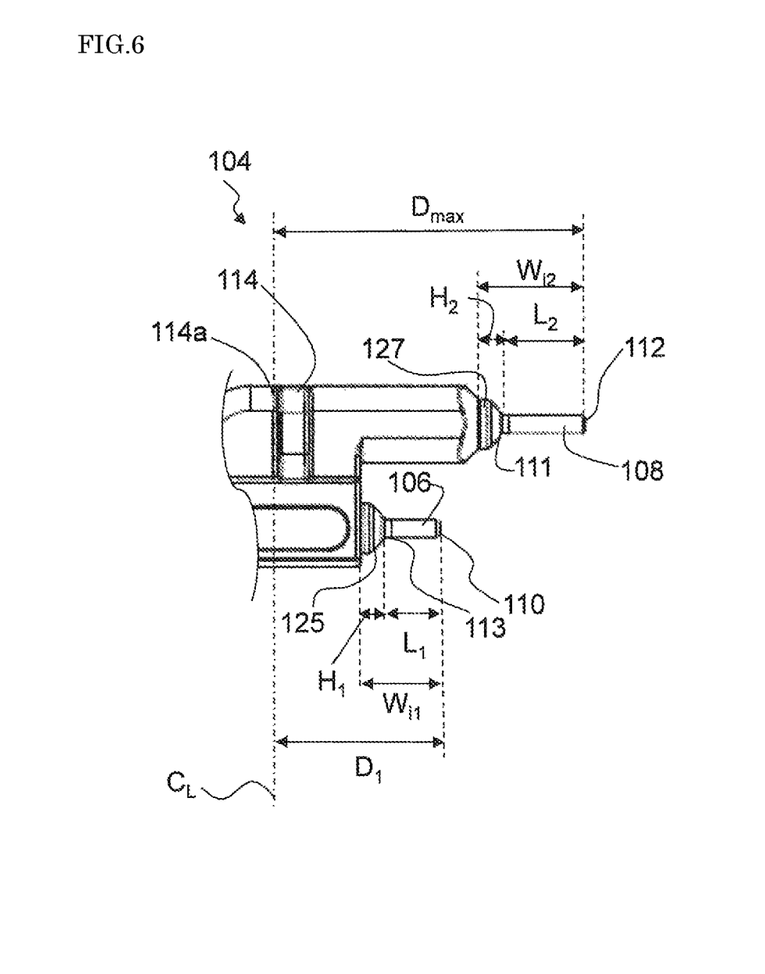
FIG. 6 is a partially enlarged view of the connection plug shown in FIG. 4A.

In a preferred embodiment, when the connection plug 104 is designed to be connected such that a portion with the shortest distance $D_{max}$ between the foremost end of the connection plug 104 (the leading end 112 of the second connection terminal 108) and a base end 114a on the connection terminal side of the flange 114 is inserted into the receiving port of the relay apparatus, it is preferable to design the connection plug 104 such that a total $W_{i2}$ of the axial length $L_2$ of the second connection terminal 108 and a dome height $H_2$ of the second dome-shaped protrusion 127 is smaller than the shortest distance $D_1$ between a boundary line $C_L$ formed when the connection plug 104 is inserted into the receiving ports of the relay apparatus to the depth corresponding to the above-mentioned $D_{max}$ in the axial direction of the second connection terminal 108, and the leading end 110 of the first connection terminal 106 ($W_{i2} < D_1$). When the relationship $W_{i2} < D_1$ is satisfied, even if the second connection terminal 108 is mistakenly inserted into a receiving port of the relay apparatus that corresponds to the first connection terminal 106, the leading end 112 of the second connection terminal 108 cannot reach (i.e., cannot come into contact with) a component inside the relay apparatus that is provided for the contact with the leading end of the first connection terminal, and thus a risk that the leading end 112 of the second connection terminal 108 and the component inside the relay apparatus will be contaminated or damaged due to improper insertion can be eliminated.

Alternatively, in a preferred embodiment, it is preferable to design the connection plug 104 such that the total $W_{i2}$ of the axial length $L_2$ of the second connection terminal 108 and the dome height $H_2$ of the second dome-shaped protrusion 127 is smaller than a total $W_{i1}$ of the axial length $L_1$ of the first connection terminal 106 and a dome height $H_1$ of the first dome-shaped protrusion 125 ($W_{i2} < W_{i1}$). Also in this case, when the relationship $W_{i2} < W_{i1}$ is satisfied, even if improper insertion into the receiving port of the relay apparatus is performed, the leading end 112 of the second connection terminal 108 cannot reach (i.e., cannot come into contact with) a component inside the relay apparatus that is provided to come into contact with the leading end of the first connection terminal, and thus a risk that the component inside the relay apparatus will be damaged due to improper insertion can be eliminated.

1.2 Catheter Portion of Flexible Endoscope

In the flexible endoscope 100 of the present invention shown in FIG. 1, the length of the catheter portion 102 is not particularly limited, but the catheter portion 102 is designed to preferably have a length of 1000 mm to 2500 mm, and more preferably 1200 mm to 2300 mm. In contrast, the catheter portion 102 preferably has an average outer diameter of 0.3 mm to 3 mm, and more preferably 0.5 mm to 2 mm.

Figure 7A:
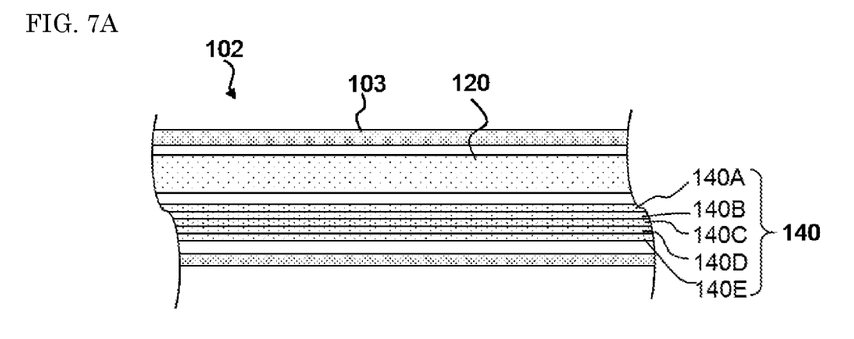
FIG. 7A is a cross-sectional view of the intermediate portion of the catheter portion.
Figure 7B:
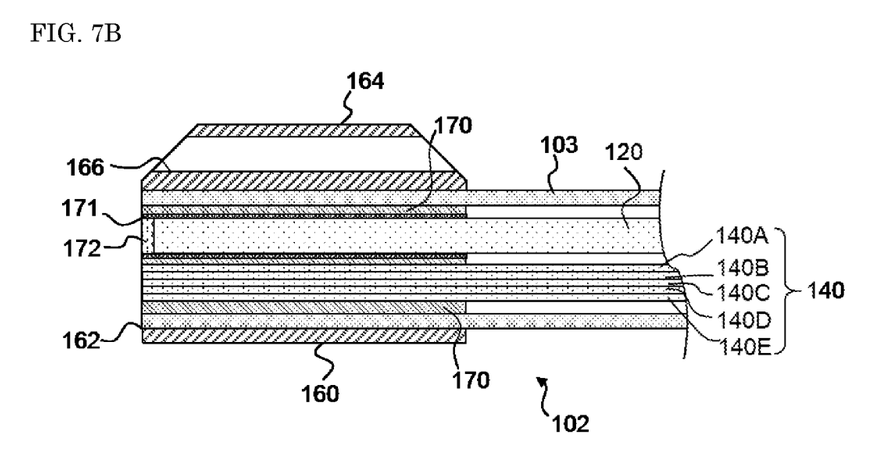
FIG. 7B is a cross-sectional view of the distal end portion of the catheter portion.

FIGS. 7A and 7B show cross-sectional views of the catheter portion 102 included in the flexible endoscope shown in FIG. 1 in the longitudinal direction. FIG. 7A is a cross-sectional view of the intermediate portion of the catheter portion 102 in a range indicated by mark A in FIG. 1, and FIG. 7B is a cross-sectional view of the distal end portion of the catheter portion 102 in a range indicated by mark B in FIG. 1.

With an embodiment of the present invention, in the intermediate portion of the catheter portion 102, the image guide 120 and the light guide 140 are arranged inside the catheter tube 103 as shown in FIG. 7A without being bonded together.

The catheter tube 103 is made of a material such as polyimide, fluororesin, PTFE (polytetrafluoroethylene), nylon, polyurethane, polypropylene, or vinyl chloride, and preferably has an average inner diameter of 0.1 mm to 3 mm, and more preferably 0.2 mm to 0.7 mm.

The image guide 120 includes a single image fiber that is elongated and substantially cylindrical, for example. Specific examples of the image fiber include known image fibers for image transmission (e.g., those obtained by regularly arranging preferably 8000 to 20000 glass fibers and bundling them, or bundling and bonding them, or by extending the thus-obtained bundles). The image guide 120 preferably has an average outer diameter of 0.05 mm to 1 mm, and more preferably 0.1 mm to 0.5 mm.

The light guide 140 includes a plurality of optical fibers that are elongated and substantially cylindrical, for example. Specific examples of the optical fibers include known lighting fibers. Each of the optical fibers preferably has an average outer diameter of 0.001 mm to 1 mm, and more preferably 0.01 mm to 0.1 mm. In the intermediate portion of the light guide 140 (i.e., a portion of the light guide 140 other than a portion near the distal end and a portion near the proximal end), for example, these optical fibers are held in a state in which they are not bonded together. The light guide 140 preferably includes 1 to 100 optical fibers, and more preferably 10 to 50 optical fibers. It should be noted that, in FIG. 7A, the light guide 140 includes optical fibers 140A, 140B, 140C, 140D, and 140E, and is spaced apart from the image guide 120, but there is no limitation to this configuration. For example, the optical fibers 140A, 140B, 140C, 140D, and 140E included in the light guide 140 may be distributed around the image fiber 120 and arranged in a circular shape, for example.

With an embodiment of the present invention, the image guide 120 and the light guide 140 are bonded together with the catheter tube 103 and a lens tube 171 and a lens 172, which will be described later, using an adhesive material 170 such as an epoxy-based adhesive in the distal end portion of the catheter portion (FIG. 7B).

As described above, with the present invention, the image guide 120 and the light guide 140 are integrated through bonding or fixing in both the distal end portion and the proximal end portion, whereas the image guide 120 and the light guide 140 are not bonded together in the intermediate portion, and they can thus be curved individually. This makes it possible to disperse stress applied to the catheter portion in the longitudinal direction.

Furthermore, with an embodiment of the present invention, as shown in FIG. 7B, the end fitting 160 is provided around the outer circumference of the catheter tube 103 in the distal end portion of the catheter portion. The end fitting 160 is provided with a first through hole 162 through which the distal end portion of the catheter tube 103 passes and that is in intimate contact with the outer circumferential surface of the distal end portion of the catheter tube 103. The end fitting 160 includes a protruding portion 164 on a portion of the outer circumference, and the protruding portion 164 is provided with a second through hole 166 extending substantially in parallel with the first through hole 162. The second through hole 166 is used to pass a guide wire (not shown) that can be used together with the flexible endoscope of the present invention therethrough. The average inner diameter of the first through hole 162 can be selected such that its size corresponds to the average outer diameter of the used catheter tube 103, for example. The average inner diameter of the second through hole 166 is not particularly limited, and can be selected from sizes that allow the used guide wire to pass and move therethrough, with consideration given to the average inner diameter of the guide wire. The end fitting 160 is made of a material such as metal (e.g., stainless steel, an aluminum alloy, a platinum-based alloy, titanium, or gold) or ceramic, for example.

In the distal end portion of the catheter portion 102, the leading end (distal end) of the image guide 140 is provided with the lens 172 as needed. Furthermore, the image guide 140 and the lens 172 may be surrounded by the lens tube 171 in the axial direction in order to impart sufficient strength to the distal end portion. On the other hand, in FIG. 7B, the light guide 140 includes optical fibers 140A, 140B, 140C, 140D, and 140E, and is spaced apart from the image guide 120, but there is no limitation to this configuration. For example, the optical fibers 140A, 140B, 140C, 140D, and 140E included in the light guide 140 may be arranged around the image fiber 120 in a dispersed manner, for example.

The flexible endoscope of the present invention includes the connection plug and the catheter portion as described above, and can be used as an angioscope, a ureteroscope, or a falloposcope, for example. The flexible endoscope of the present invention is preferably an angioscope.

2. Endoscope System

Figure 8:
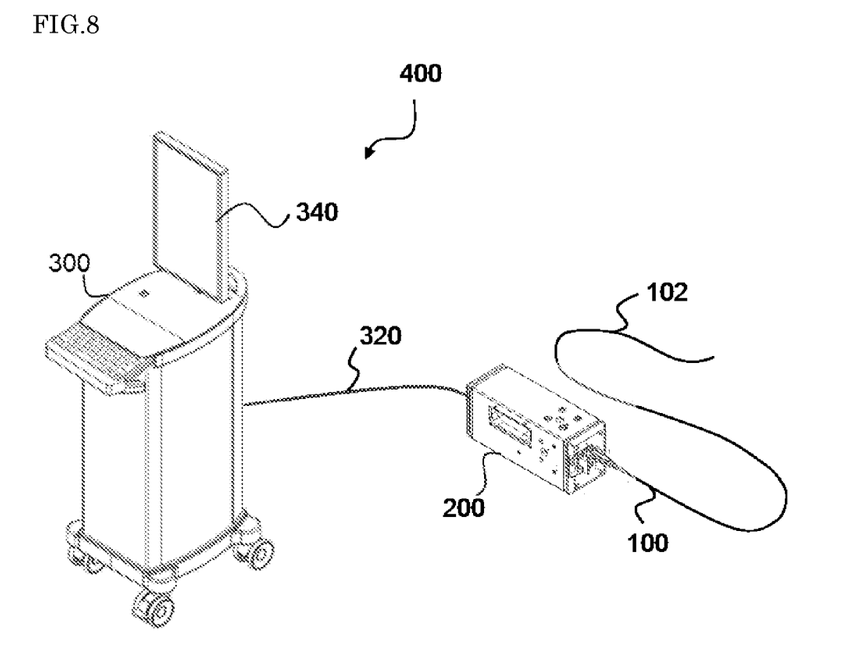
FIG. 8 is a diagram showing an example of an endoscope system in which the flexible endoscope of the present invention shown in FIG. 1 is connected to a relay apparatus and a medical console.

FIG. 8 is a diagram showing an example of an endoscope system in which the flexible endoscope of the present invention shown in FIG. 1 is connected to a relay apparatus and a medical console.

As shown in FIG. 8, the flexible endoscope 100 of the present invention is connected to a relay apparatus 200 via the connection plug. Furthermore, the relay apparatus 200 is connected to a medical console 300 via a cable 320. An endoscope system 400 is thus constructed.

With the endoscope system 400 of the present invention, a doctor can move the catheter portion 102 of the flexible endoscope 100 to a desired position through a blood vessel of a patient, for example, and use the relay apparatus 200 to display an image of the lesion obtained at the distal end of the catheter portion 102 on a display 340 of the medical console 300. At this time, the doctor can instruct the medical console through the operation of buttons provided in the relay apparatus 200 to enlarge and reduce an image displayed on the display, adjust brightness, and start and stop recording the image or reproduce a recorded image.

It should be noted that the embodiment in which the relay apparatus 200 and the medical console 300 are connected via the cable 320 has been described above, but the present invention is not limited to only such an embodiment. For example, the relay apparatus is not connected to the console via the above-mentioned cable 320, but the components of the relay apparatus are directly incorporated into the console to form a console apparatus as a whole. That is, such a console apparatus can also form an endoscope system together with the flexible endoscope of the present invention. In this case, the connection plug of the flexible endoscope is connected to the console apparatus via a receiving port provided in the console apparatus.

LIST OF REFERENCE NUMERALS

100 flexible endoscope
102 catheter portion
103 catheter tube
104 connection plug 105, 105' hollow cover
106 first connection terminal
107 flexible tube
108 second connection terminal
120 image guide
140 light guide
152, 154 boss
160 end fitting
162 first through hole
164 protruding portion
166 second through hole
170 adhesive material
200 relay apparatus
300 medical console
400 endoscope system

What is claimed is:

1. An angioscope comprising:
a catheter portion; and
a connection plug,
wherein the catheter portion includes an image guide, a light guide, and a catheter tube that surrounds the image guide and the light guide in a longitudinal direction,
the connection plug includes a hollow cover that accommodates a proximal end of the catheter tube, a flexible tube that protrudes from the hollow cover and through which the catheter tube is passed, a first connection terminal that is connected to the light guide extending from the proximal end of the catheter tube, and a second connection terminal that is connected to the image guide extending from the proximal end of the catheter tube,
the image guide and the light guide are slidable inside the catheter tube,
the first connection terminal and the second connection terminal protrude from end portions of the hollow cover of the connection plug, and protruded portions of the first connection terminal and the second connection terminal are disposed substantially in parallel to each other, and
at least one of the image guide and the light guide is arranged curved inside the hollow cover of the connection plug.

2. The angioscope according to claim 1, wherein a level difference is formed between a leading end of the first connection terminal protruding from the hollow cover and a leading end of the second connection terminal protruding from the hollow cover.

3. The angioscope according to claim 2, wherein the leading end of the second connection terminal is positioned farther than the leading end of the first connection terminal.

4. The angioscope according to claim 1, wherein at least one flange extending in a direction orthogonal to an arrangement direction of the first connection terminal and the second connection terminal is provided on an outer surface of the hollow cover.

5. The angioscope according to claim 1, wherein at least one boss is provided on an inner surface of the hollow cover of the connection plug, and at least one of the light guide and the image guide circumvents the boss in the hollow cover and is thus arranged curved.

6. The angioscope according to claim 1, wherein, in the hollow cover of the connection plug, the image guide is arranged curved, and the light guide is substantially linearly arranged.

7. The angioscope according to claim 1, wherein, in the connection plug, a portion on the first connection terminal side and a portion on the second connection terminal side differ in thickness.

8. An endoscope system comprising:
the angioscope according to claim 1;
a relay apparatus connected to the first connection terminal and the second connection terminal of the angioscope, wherein the first connection terminal and the second connection terminal of the angioscope are located inside the relay apparatus; and
a console that is connected to the relay apparatus via a cable for transmitting image information.

* * * * *